United States Patent
Kim et al.

(10) Patent No.: US 9,926,223 B2
(45) Date of Patent: Mar. 27, 2018

(54) DENTAL GLASS-CERAMICS BLOCK BONDED WITH ABUTMENT AND PREPARATION METHOD THEREOF

(71) Applicant: HASS CO., LTD., Gangneung-si (KR)

(72) Inventors: Yong su Kim, Gangneung-si (KR); Hyun jun Jeon, Busan (KR); Hyung Bong Lim, Ansan-si (KR); Kyung Sik Oh, Incheon (KR); Sung ho Ha, Ansan-si (KR); Young pyo Hong, Gangneung-si (KR); Joon hyung Kim, Ansan-si (KR); Cheol young Kim, Seoul (KR)

(73) Assignee: HASS CO., LTD., Gangneung-si, Gangwon-do (KR)

(*) Notice: Subject to any disclaimer, the term of this patent is extended or adjusted under 35 U.S.C. 154(b) by 0 days.

(21) Appl. No.: 15/155,752

(22) Filed: May 16, 2016

(65) Prior Publication Data
US 2017/0057865 A1    Mar. 2, 2017

(30) Foreign Application Priority Data
Aug. 26, 2015   (KR) .................. 10-2015-0120264

(51) Int. Cl.
*C03C 10/00*    (2006.01)
*A61K 6/00*    (2006.01)
(Continued)

(52) U.S. Cl.
CPC ........ *C03C 10/0027* (2013.01); *A61K 6/0005* (2013.01); *A61K 6/024* (2013.01);
(Continued)

(58) Field of Classification Search
CPC ................... C03C 10/0027; C03C 10/0014
(Continued)

(56) References Cited

U.S. PATENT DOCUMENTS 5,219,799 A * 6/1993 Beall .................. C03C 10/0009
                                                                 501/5
5,702,514 A   12/1997 Petticrew
(Continued)

FOREIGN PATENT DOCUMENTS

EP          0827941 A1      3/1998
EP          1534169         3/2006
(Continued)

OTHER PUBLICATIONS

Borom et al. "Strength and Microstructure in Lithium Disilicate Glass-Ceramics", Journal of the American Ceramic Society, Mar. 17, 1975, vol. 58(9-10), pp. 385-391 (Presented at the Pacific Coast Regional Meeting, The American Ceramic Society, San Francisco, CA, Oct. 31, 1973).

*Primary Examiner* — Noah Wiese
(74) *Attorney, Agent, or Firm* — Novick, Kim & Lee, PLLC; Sang Ho Lee

(57) ABSTRACT

A method of bonding a high-strength zirconia post serving as a core in a glass-ceramic block, a method of bonding a metal link fastened with an implant fixture to the zirconia post, and glass-ceramic bondable to the zirconia post and a preparation method thereof, when preparing artificial teeth through a CAD/CAM processing method by using the glass-ceramic block as an artificial-teeth material. The lithium disilicate glass-ceramics containing cristobalite crystalline includes glass-ceramics composition including 10 to 15 wt % $Li_2O$, 68 to 76 wt % $SiO_2$, 2 to 5 wt % $P_2O_5$ working as a nuclei formation agent, 0 to 5 wt % $Al_2O_3$ to increase glass transition temperature and softening temperature and increase chemical durability of the glass, 2 to 3 wt % $ZrO_2$, 0.5 to 3 wt % CaO for enhancing a thermal expansion coefficient of the glass, 0.5 to 5 wt % $Na_2O$, 0.5
(Continued)

to 5 wt % $K_2O$, and 1 to 2 wt % colorants, and 0 to 2.0 wt % mixture of MgO, ZnO, F, and $La_2O_3$.

4 Claims, 3 Drawing Sheets

(51) Int. Cl.
    *A61K 6/02* (2006.01)
    *A61K 6/027* (2006.01)
    *C03C 3/097* (2006.01)
    *C03B 32/02* (2006.01)
    *C03B 23/20* (2006.01)
    *C03C 4/00* (2006.01)
    *C03C 8/24* (2006.01)
    *C04B 37/00* (2006.01)

(52) U.S. Cl.
    CPC .......... *A61K 6/0273* (2013.01); *C03B 23/20* (2013.01); *C03B 32/02* (2013.01); *C03C 3/097* (2013.01); *C03C 4/0021* (2013.01); *C03C 8/24* (2013.01); *C03C 10/0009* (2013.01); *C04B 37/00* (2013.01); *C03C 2204/00* (2013.01)

(58) Field of Classification Search
    USPC .................................................... 501/5, 6, 7
    See application file for complete search history.

(56) References Cited

U.S. PATENT DOCUMENTS

| | | | |
|---|---|---|---|
| 6,372,319 | B1 | 4/2002 | Abe et al. |
| 6,818,573 | B2 * | 11/2004 | Petticrew ............... A61C 13/20 106/35 |
| 9,409,816 | B2 * | 8/2016 | Kim .................... C03C 10/0027 |
| 2006/0099552 | A1 | 5/2006 | Van Der Zel et al. |
| 2007/0042889 | A1 | 2/2007 | Apel et al. |
| 2014/0370464 | A1 * | 12/2014 | Kounga ................. A61C 13/00 433/212.1 |
| 2015/0104655 | A1 | 4/2015 | Kim et al. |

FOREIGN PATENT DOCUMENTS

| | | |
|---|---|---|
| EP | 3015436 A1 | 5/2016 |
| KR | 10-2015-0043633 A | 4/2015 |

\* cited by examiner

DENTAL GLASS-CERAMICS BLOCK BONDED WITH ABUTMENT AND PREPARATION METHOD THEREOF

CROSS-REFERENCE TO RELATED APPLICATION

This application claims priority from and the benefit of Korean Patent Application No. 10-2015-0120264, filed on Aug. 26, 2015, which is hereby incorporated by reference for all purposes as if fully set forth herein.

BACKGROUND

Field

Exemplary embodiments relate to preparing artificial teeth through a computer aided design (CAD) or computer aided manufacturing (CAM) method by using a glass-ceramic block as an artificial-teeth material. In particular, exemplary embodiments relate to a method of bonding a high-strength zirconia post serving as a core in the glass-ceramic block. In addition, exemplary embodiments relate to a method of bonding a metal link with an implant fixture to the zirconia post and the glass-ceramic bondable to the zirconia post and a preparation method thereof.

Discussion of the Background

With economic development and increased consumer income, consumers have an increased interest in appearance. In response to consumers increased interest in appearance, researchers have increased their interest in the aesthetics of dental prosthetic materials. As a result, researchers have introduced various kinds of dental prosthetic restoration materials such as various non-metal crown materials.

Crown materials refer to prosthetic materials for restoring enamel and dentin parts of a damaged tooth. The crown materials are classified into inlay, onlay, veneer, and crown according to an applied region. Since the region restored by the crown material is the outer surface of the tooth, consumers demand that these materials closely resemble natural teeth in color, texture, and overall appearance. In addition, the crown materials must be high strength materials to prevent fracturing (e.g., abrasion and chipping). Common crown materials include aleucite glass-ceramic, a reinforced porcelain, or a fluorapatite ($Ca_5(PO_4)_3F$) glass-ceramic. Although these common crown materials may closely resemble natural teeth, these materials are highly susceptible to factures. In other words, these common crown materials are low strength materials and may fracture under an applied pressure of about 80 mega pascals (MPa) to 120 MPa.

A lithium silicate glass-ceramic was introduced by Marcus P. Borom and Anna M. Turkalo. See Marcus P. Borom and Anna M. Turkalo (The Pacific Coast Regional Meeting, The American Ceramic Society, San Francisco, Calif., Oct. 31, 1973 (Glass division, No. 3-G-73P)), abstract. The formation of various crystalline nuclei and the crystalline and the strength for each growth heat treatment condition were studied by using $Li_2O$—$Al_2O_3$—$SiO_2$—$Li_2O$—$K_2O$—$B_2O_3$—$P_2O_5$-based glass. The strength of a high-temperature lithium disilicate crystalline and a low-temperature lithium metasilicate varies from 30 to 35 kPSI. The strength is caused by residual stress due to a difference in thermal expansion coefficient between base glass, mother glass, $Li_2SiO_5$, and $Li_2SiO_3$ crystals.

Materials and methods of preparing monolithic dental crowns by glass including lithium disilicate crystal are known (see European Patent No. 1 534 169 B1, filed Sep. 3, 2003). However, applying glass-ceramic material to a tri-layered block by bonding zirconia and metals is not known. The glass-ceramic material needs to be matched with the thermal expansion coefficient of zirconia, and respective inorganic bonds capable of bonding between the glass-ceramic and zirconia and between the zirconia and metal are important elements.

That is, in the related art, the glass-ceramic block is bonded with the metallic link to be applied to the implant aesthetic prosthesis, and in this case the metallic link can cause an allergic reaction with an individual having the implanted aesthetic prosthesis. Further, since the metal and the glass-ceramic are bonded with each other, fracture or bonding in an interface is not facilitated by a property difference between the two materials.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a glass-ceramic material which is bondable with zirconia.

Exemplary embodiments provide an inorganic bond which thermally bonds glass-ceramic materials which are bondable with zirconia.

Exemplary embodiments provide an abutment glass-ceramic block with high strength and aesthetic properties by bonding high-strength zirconia to an internal core.

Exemplary embodiments provide a lithium silicate glass-ceramic comprising a glass composition including 10 to 15 wt % $Li_2O$, 68-76 wt % $SiO_2$, 2 to 5 wt % $P_2O_5$ working as a nuclei formation agent, 0 to 5 wt % $Al_2O_3$ to increase chemical durability of the glass, 2 to 3 wt % $ZrO_2$, 0.5 to 3 wt % CaO for enhancing a thermal expansion coefficient of the glass, 0.5 to 5 wt % $Na_2O$, 0.5 to 5 wt % $K_2O$, and 1 to 2 wt % colorants, and 0 to 2.0 wt % mixture of MgO, ZnO, F, and $La_2O_3$.

Exemplary embodiments provide a lithium disilicate glass-ceramic containing cristobalite crystalline comprising a glass-ceramic composition including 10 to 15 wt % $Li_2O$, 68 to 76 wt % $SiO_2$, 2 to 5 wt % $P_2O_5$ working as a nuclei formation agent, 0 to 5 wt % $Al_2O_3$ to increase glass transition temperature and softening temperature and increase chemical durability of the glass, 2 to 3 wt % $ZrO_2$, 0.5 to 3 wt % CaO for enhancing a thermal expansion coefficient of the glass, 0.5 to 5 wt % $Na_2O$, 0.5 to 5 wt % $K_2O$, and 1 to 2 wt % colorants, and 0 to 2.0 wt % mixture of MgO, ZnO, F, and $La_2O_3$.

Exemplary embodiments provide a preparation method of a lithium disilicate glass-ceramic containing cristobalite crystalline comprising: melting and crystallized-growing the glass-ceramic composition including 10 to 15 wt% $Li_2O$, 68-76 wt% $SiO_2$, 2 to 5 wt% $P_2O_5$, 0 to 5 wt% $Al_2O_3$, 2 to 3 wt% $ZrO_2$, 0.5 to 3 wt% CaO, 0.5 to 5 wt% $Na_2O$, 0.5 to 5 wt% $K_2O$, and 1 to 2 wt% colorants, and 0 to 2.0 wt% mixture of MgO, ZnO, F, and $La_2O_3$; and performing first crystallization heat treatment at 700° C. to 900° C. for 1 minute to 2 hours.

The inorganic bond may include 8 to 12 wt % $Li_2O$, 50 to 75 wt % $SiO_2$, 0 to 3 wt % $Al_2O_3$, 0.5 to 5 wt % CaO, 0.5 to 3 wt % $Na_2O$, 0.5 to 3 wt % $K_2O$, 0.5 to 7 wt % $P_2O_5$ as a nuclei formation agent, 0.5 to 1 wt % colorant, and 0 to 1.0 wt % mixture of MgO, ZnO, F, and $La_2O_3$, and the thermal expansion coefficient is 9.5 to $10.8 \times 10^{-6}$/° C.

The glass-ceramic for bonding zirconia and the inorganic bond according to various exemplary embodiments can be used to prepare a crown prosthetic material including metal link/zirconia post/glass-ceramic that has high resistance to fracture and is similar in texture and color to a natural tooth.

Further, the inorganic bond cannot be produced if the glass-ceramic has a different thermal expansion coefficient of zirconia, but the inorganic bond proposed in the exemplary embodiments is formed with a uniform and dense structure between zirconia and the glass-ceramic to reduce the possibility of secondary infection caused by bacteria penetration as well as increase mechanical stability by reinforcing the bond strength between the two materials.

Additional aspects will be set forth in the detailed description which follows, and, in part, will be apparent from the disclosure, or may be learned by practice of the inventive concept.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

Figure 1:
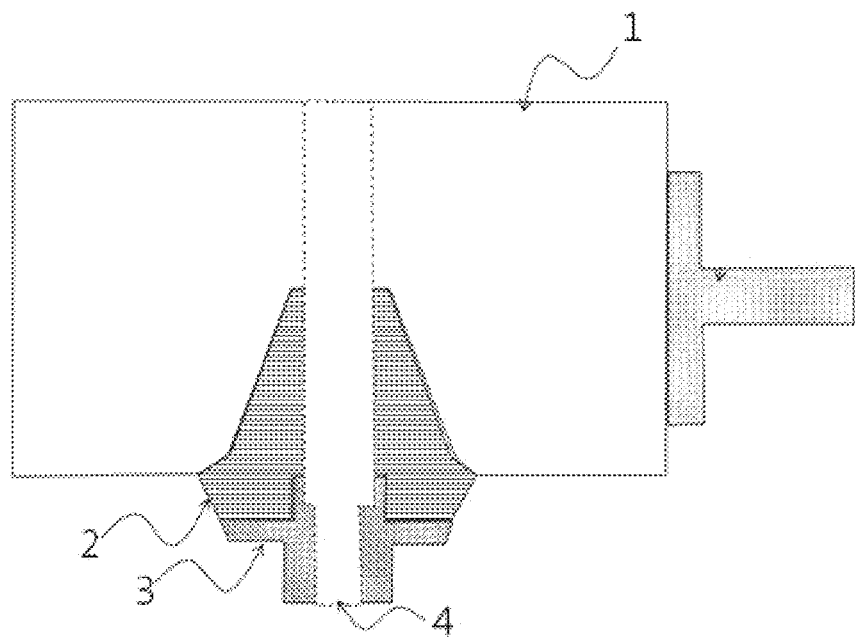
FIG. 1 is a schematic diagram of a CAD- or CAM-processed aesthetic prosthetic block to which three materials of a glass-ceramic, zirconia, and a metal are applied according to an exemplary embodiment.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements.

In the accompanying figures, the size and relative sizes of components or elements may be exaggerated for clarity and descriptive purposes.

When an element or component is referred to as being "on" another element or component, it may be directly on the other element or component or intervening elements or components may be present. When, however, an element or component is referred to as being "directly on," another element or component, there are no intervening elements or components present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

A dental high-strength glass-ceramic according to various exemplary embodiments includes at least one of cristobalite, lithium disilicate crystal, and a glassy material. The dental high-strength glass-ceramic entirely has a very similar color and texture to natural human teeth. Thus, the aesthetics of these materials match the aesthetics of natural teeth.

The aesthetics, particularly, light transmittance is largely affected by the degree of light scattering caused by a difference in refractive index between different crystal lines in dense bulk. The refractive index of cristobalite is 1.48. As the content of cristobalite increases, the interfaces with mother glass or lithium disilicate crystalline increases, and thus, the scattering of light is increased to reduce the transmittance. Therefore, only an appropriate amount of cristobalite crystalline needs to be formed in the glass so as to have light transmittance matching natural teeth.

The strength of the glass-ceramic may be improved by compressive stress formed on phases with different thermal expansion coefficients. The thermal expansion coefficient of cristobalite is known to be $10.9 \times 10^{-6}/°C$. (F, Aumento, The American Mineralogist, vol. 51, July, 1966), and the thermal expansion coefficient of the lithium disilicate is known to be $11.4 \times 10{-6}/°C$. (Marcus P. Borom, Journal of The American Ceramic Society, vol. 58, no. 9-10, 1975). Therefore, in order to induce the compressive stress in the mother glass, it is important that a glass composition is designed to have a lower thermal expansion coefficient than that of cristobalite crystalline.

Further, the lithium disilicate glass-ceramic of various exemplary embodiments may have a higher biaxial strength than the strength of the existing lithium disilicate glass-ceramic (i.e., approximately 350 MPa). Thus, the lithium disilicate glass-ceramic may be applicable as an aesthetic prosthetic material in terms of light transmittance. The glass or the glass-ceramic may be monolithically applicable to single crowns and bridges. The glass or the glass ceramic may be bonded to the top of heavy portions of zirconia, such as posterior or bridges. In this case, the bond strength on a bond interface between zirconia and lithium disilicate glass-ceramic has a tensile bond strength twice that of the bond strength of porcelain fused to metal (PFM).

Hereinafter, CAD/CAM designed glass-ceramic bonded with a zirconia post and a preparation method of an inorganic bond according to an exemplary will be described.

The dental high-strength glass-ceramic according to an exemplary embodiment is a glass-ceramic including at least one of lithium disilicate crystal, cristobalite, and lithium phosphate crystal. The glass for enhancing the strength and the aesthetic light transmittance may include a glass-ceramic composition including 10 to 15 wt % lithium oxide ($Li_2O$), 68 to 76 wt % silicon dioxide ($SiO_2$), 2 to 5 wt % phosphorus pentoxide ($P_2O_5$) working as a nuclei formation agent, 0 to 5 wt % aluminum oxide ($Al_2O_3$) to increase a glass transition temperature and a softening point and increase chemical durability of the glass, 2 to 3 wt % zirconium dioxide ($ZrO_2$), 0.5 to 3 wt % calcium oxide (CaO) for enhancing a thermal expansion coefficient of the glass, 0.5 to 5 wt % sodium oxide ($Na_2O$), 0.5 to 5 wt % potassium oxide ($K_2O$), and other colorants are included with 1 to 2 wt % and magnesium oxide (MgO), zinc oxide (ZnO), fluorine (F), and lanthanum oxide ($La_2O_3$) are mixed and added with 0 to 2.0 wt % due to the effect on light transmittance. Alkali oxide may be potassium oxide ($K_2O$) or sodium oxide ($Na_2O$), and further, may include both potassium oxide and sodium oxide.

The dental high-strength glass-ceramic according to an exemplary embodiment further includes 1 to 2 wt % colorant as described above in order to provide the same or similar color as natural teeth. The colorant may provide the same or similar color and fluorescence as natural teeth. The colorant may include at least one of red iron oxide ($Fe_2O_3$), yellow ceria ($CeO_2$), orange vanadium pentoxide ($V_2O_5$), black vanadium trioxide ($V_2O_3$), erbium(III) oxide ($Er_2O_3$), terbium(III) oxide ($Tb_2O_3$), praseodymium(III) oxide ($Pr_2O_3$), titanium oxide ($TiO_2$), tantalum (IV) oxide $TaO_2$, manganese dioxide ($MnO_2$). For example, red iron oxide ($Fe_2O_3$), ceria ($CeO_2$), or vanadium pentoxide ($V_2O_5$) may be mixed together with starting materials and melted to achieve a material having a yellow tint similar to natural human teeth. Titanium oxide ($TiO_2$) may be used to achieve a white tint similar in color to natural teeth.

The aforementioned starting materials may be measured and mixed. In this case, lithium carbonate ($Li_2CO_3$) instead of lithium oxide ($Li_2O$) may be added and carbon dioxide ($CO_2$) as a carbon (C) component of lithium carbonate ($Li_2CO_3$) may be discharged and removed as gas in a melting process of the glass. Further, in alkali oxide, potassium carbonate ($K_2CO_3$) and sodium carbonate ($Na_2CO_3$) instead of potassium oxide ($K_2O$) and sodium oxide ($Na_2O$) may be added, respectively, and carbon dioxide ($CO_2$) as carbon (C) components of potassium carbonate ($K_2CO_3$) and sodium carbonate ($Na_2CO_3$) is discharged and removed as gas in a melting process of the glass.

The mixing process may include a dry mixing process. For example, a ball milling process may be used as the dry mixing process. The ball milling process may involve providing the starting materials in a ball milling machine, mechanically grinding and uniformly mixing the starting materials by rotating the ball milling machine at a predetermined speed. The balls used in the ball milling machine may include ceramic materials such as zirconia or alumina. Balls of the same size may be used in the ball milling process or balls of different sizes may be used. The size of the ball, milling time, rotation in revolutions per second (rpm) of the ball milling machine, may be controlled based on a desired size of the final particle. For example, the size of the ball may be set in a range of approximately 1 mm to 30 mm, and the rotation of the ball milling machine may be set in a range of approximately 50 to 500 rpm to achieve a final particle of a desired size. The ball milling may be performed 1 to 48 hours to achieve a product of a desired size. The starting materials may be grinded to micro-sized particles, have uniform particle sizes, and be uniformly mixed at the same time.

The mixed starting material may be put in a melting furnace and melted by heating the melting furnace with the starting material. Herein, the "melting" means that the starting materials change from a solid state to a liquid state or a material in liquid state decreases in viscosity. It is preferred that the melting furnace is made of a material having a high melting point, a large strength, and a low contact angle in order to suppress a molten material from being attached. To this end, it is preferred that the melting furnace includes a melting furnace made of a material such as platinum (Pt), diamond-like-carbon (DLC), and chamotte or coated on the surface with a material such as platinum (Pt) or diamond-like-carbon (DLC).

The furnace may melt the starting materials by heating the starting materials. The furnace may be heated to 1,400° C. to 2,000° C. and sustain a temperature in this range for 1 to 12 hours at atmospheric pressure. If a temperature of the furnace is less than 1,400° C., the starting materials may not melt. If the starting materials require a melting temperature of more than 2,000° C. and the furnace is required to reach 2,000° C. or more, then the starting materials are not economic due to excessive energy consumption. Thus, it is preferred that the starting materials melt at 1,400° C. to 2,000°. Further, when the melting time is too short (e.g., less than 1 hour), the starting materials may not sufficiently melt. When the melting time is very large (e.g., more than 12 hours), the starting materials are not economic due to excessive energy consumption. It is preferred that the heating rate of the melting furnace is 5 to 50° C./min. When the heating rate of the melting furnace is very slow (e.g., less than 5° C./min), productivity deteriorates. When the heating rate of the melting furnace is very fast (e.g., more than 50° C./min), the amount of the volatile starting materials increase resulting in unfavorable glass-ceramic properties. As a result, it is preferred that the temperature of the melting furnace be increased at a rate of 5 to 50° C./min. It is preferred that the melting is performed at an oxygen atmosphere such as air.

In order to obtain the dental glass-ceramic having a desired shape and size, the molten material may be poured in a predetermined mold. It is preferred that the mold is made of a material having a high melting point, high strength, and a low contact angle for suppressing the glass molten material from being attached. To this end, the mold may include a material such as graphite and carbon and the molten material be preheated at 200 to 300° C. and poured in the mold to prevent thermal shock.

The molten material contained in the mold may be cooled and transferred to a crystallization heat-treatment furnace to perform nuclei formation and crystal growth of the glass. In the first heat treatment, the crystallization heat treatment may be performed at 700 to 900° C. and a holding time may be 1 minute to 2 hours. Since the second heat treatment process may be a selective process, the glass-ceramic may be immediately applied to the prosthesis after processing without the second heat treatment process after the first heat treatment, or applied to the prosthesis after increasing the strength by increasing the crystal growth through the second heat treatment process. In this case, the second heat treatment process may be performed for the holding time of 1 minute to 2 hours at 800 to 920° C., and the second heat treatment may be selectively determined by customers by considering a strength requirement degree, time constraints of the prosthesis preparing process, and the like.

When the first heat treatment temperature is less than 700° C., the inorganic bond may not melt due to the low temperature. Thus, zirconia and glass may not bond with each other resulting in a low strength glass-ceramic. When the first heat treatment temperature is 900° C. or more, the size of nuclei may increase. Thus, the processing the glass ceramic may be difficult causing a deformation of the block. The second heat treatment process may be the selection of the customers. When the second heat treatment temperature is less than 800° C., the coarse crystal growth may not rapidly occur resulting in an inefficient second heat treatment. When the second heat treatment temperature is 920° C. or more, the deformation of the glass-ceramic occurs causing difficulties in glass-ceramic. The CAD/CAM processing is possible after the nuclei-formation heat treatment or the nuclei formation-crystal growth heat treatment and preferably after the first heat treatment. In the formed lithium disilicate crystalline, the compressive stress due to the thermal expansion coefficient of the mother glass may be applied and the mechanical process may be possible by the minute size.

When either heat treatment time is too short, the crystal growth may not sufficiently occur. When either heat treatment time is too long, the consumption of excessive energy is required, and thus, it is not economical. It is preferred that the heating rate up to the heat treatment temperature is approximately 10-60° C./min. When the heating rate is too slow (e.g., less than 10° C./min), productivity deteriorates. When the heating rate is too fast (e.g., more than 60° C./min), the amount of the volatile starting materials may increase due to the rapid temperature increase causing unfavorable properties of the glass-ceramic. As a result, it is preferred that the temperature of the melting furnace is increased at the heating rate in the aforementioned range. The heat treatment is performed at an oxygen atmosphere such as oxygen ($O_2$) and air. Atoms in the glass structure may move by heat treatment and thus, the phase transition of the glass occurs. That is, when the crystal growth occurs by the heat treatment, the crystallization including lithium silicate crystal occurs, and as a result, the glass-ceramic may be obtained.

The type of generated crystal and the content of the crystal may vary according to a heat treatment temperature. The growth of the crystal such as lithium disilicate ($Li_2Si_2O_5$), lithium phosphate ($Li_3PO_4$), and cristobalite ($SiO_2$) may occur based on the heat treatment temperature. The type of generated crystal and the content of the crystal may also vary based on the components of the starting materials and the content of the components.

The zirconia-bonded glass-ceramic block or the metal/zirconia-bonded glass-ceramic block obtained through the aforementioned crystallization heat treatment may be processed in a crown shape by cutting the block to provide a texture and shape that is similar to a natural tooth. Then, the cut block may be bonded to an implant material.

Hereinafter, a preparation method of a lithium disilicate glass-ceramic or glass to an artificial prosthesis will be described by using a squeeze casting method.

The squeeze casting may be performed by a method of pushing a glass or glass-ceramic ingot into a crown-shaped empty space positioned in an embedded material by lowering the viscosity of the glass. The viscosity of the glass is lowered by heating a furnace to a temperature of 920° C. to 1,000° C. and subjecting the glass or glass ceramic to the heat from the furnace at that temperature range. When heated, the glass phase of the glass or glass ceramic may be phase-converted into the lithium disilicate crystalline. The lithium disilicate ingot may be squeezed and may become the lithium disilicate crystalline after it is squeezed and subjected to a heat treatment. The heat treatment and squeezing causes the lithium disilicate crystalline to have a crystal shape that is elongated in a uni-axial direction.

The metal, zirconia, and glass-ceramic bonding from the inorganic bond may be simultaneously or separately performed. The bonding condition of the metal, zirconia, and glass-ceramic may be performed by subjecting the metal, zirconia, and glass-ceramic to a temperature of 700 to 900° C. for 1 minute to 2 hours as described above. The inorganic bond is the result of a highly active composition that is bondable with an inert zirconia material. For example, the highly active composition may include 8 to 12 wt % lithium oxide ($Li_2O$) having high reaction with zirconia, 50 to 70 wt % silicon dioxide ($SiO_2$) corresponding to a structural frame, 0 to 3 wt % $Al_2O_3$ to increase a glass transition temperature and a softening point and enhance chemical durability of the glass, 0.5 to 5 wt % calcium oxide (CaO) to increase the thermal expansion coefficient of the glass, 0.5 to 3 wt % sodium oxide ($Na_2O$), and 0.5 to 3 wt % potassium oxide ($K_2O$), 0.5 to 7 wt % phosphorous pentoxide ($P_2O_5$) as a nuclei formation agent for indicating the opacity when applying the colorant to the bond, and 0.5 to 1 wt % of other colorants. In addition, magnesium oxide (MgO), zinc oxide (ZnO), fluorine (F), and lanthanum oxide ($La_2O_3$) may be mixed and added with 0 to 1.0 wt % due to the effect on light transmittance. The composition of the inorganic bond may be designed to have a thermal expansion coefficient of 9.5 to $10.8 \times 10-6/°$ C. so that the thermal expansion efficient may be matched between the metal and zirconia, and between zirconia and the glass-ceramic block in addition to the chemical bond with zirconia.

The glass-ceramic for bonding zirconia and the inorganic bond according to the various exemplary embodiments include preparing the crown prosthetic material including a metal link, a zirconia post, and glass-ceramic. Previously, this was impossible for an aesthetic prosthesis using CAD/CAM processing. Exemplary embodiments have an improved bonding strength between the metal and glass-ceramic, high fracture resistance, and proper aesthetics. In particular, the inorganic bond may be chemically bonded with zirconia as an inert material through hot bonding. In addition, since the inorganic bond cannot be produced when the glass-ceramic as a thermal expansion coefficient that does not match the thermal expansion coefficient of zirconia, the glass-ceramic composition of the exemplary embodiments is used in the zirconia hot bonding method.

FIG. 1 is a schematic view of a CAD/CAM processed aesthetic prosthetic block to which a glass-ceramic block/zirconia post/metal link are applied. Hot bonding of a glass-ceramic block 1 and a zirconia post 2 may be performed by the inorganic bond. In this case, the glass-ceramic block may not deform even at a hot bonding temperature and under other processibility conditions. The glass-ceramics of the present invention maybe mechanically processed even through a hot bonding condition at 700 to 900° C. for 1 minute to 2 hours, and thereafter, light transmittance and a color which are aesthetic characteristics to be applicable as the artificial prosthetic material need to be expressed. In addition, if necessary, the glass-ceramic may be a selectable material which may be used in an application field to which higher load is applied by increasing the strength through the second crystallization heat treatment process (at 800 to 920° C. for the holding time of 1 minute to 2 hours).

A metal link 3 may be a portion bonded with the implant fixture and a screwing hole 4 may be processed inside. A conventional zirconia bond with the metal link may use a resin-based cement. However, exemplary embodiments hot bonding causes in an increased bonding force. The bonding between the metal link 3 and the zirconia post 2 may be possible even in the glass-ceramic/zirconia/metal bonding, and in order to reduce oxidation of the metal in heat treatment, the metal link can be separately bonded to the bonded glass-ceramic/zirconia at the low temperature.

The developed inorganic bond has a bonding strength that is twice larger that of the conventional adhesion between zirconia and a veneer porcelain.

Figure 2:
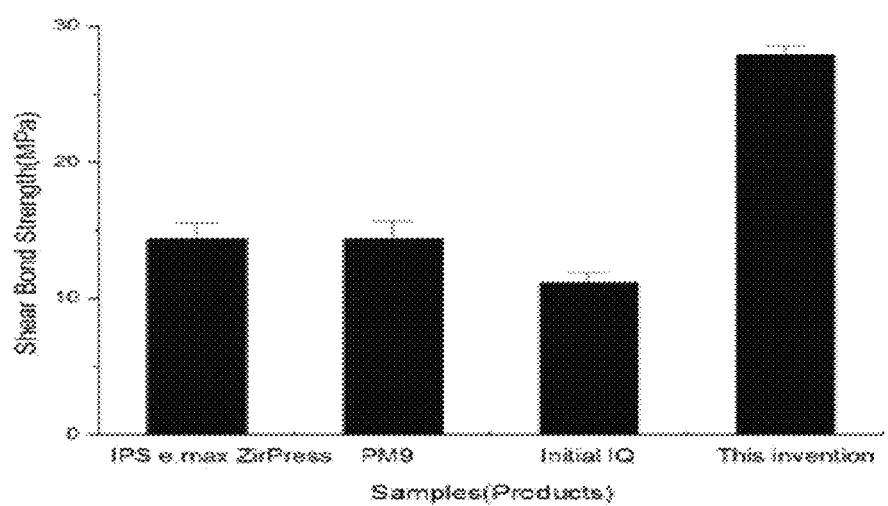
FIG. 2 is a diagram comparing the shear bond strength between zirconia and a glass-ceramic in accordance with an exemplary embodiment with the shear bond strength of existing products.

FIG. 2 illustrates shear bond strengths between an existing zirconia veneer product and a product to which an exemplary embodiment hot bonding technique is applied. As illustrated in FIG. 2, the exemplary embodiment hot bonding technique reduces the possibility of secondary infection caused by bacteria penetration as well as increases the mechanical stability of the end product due to strong bonding between two materials, as compared with existing products.

Figure 3:
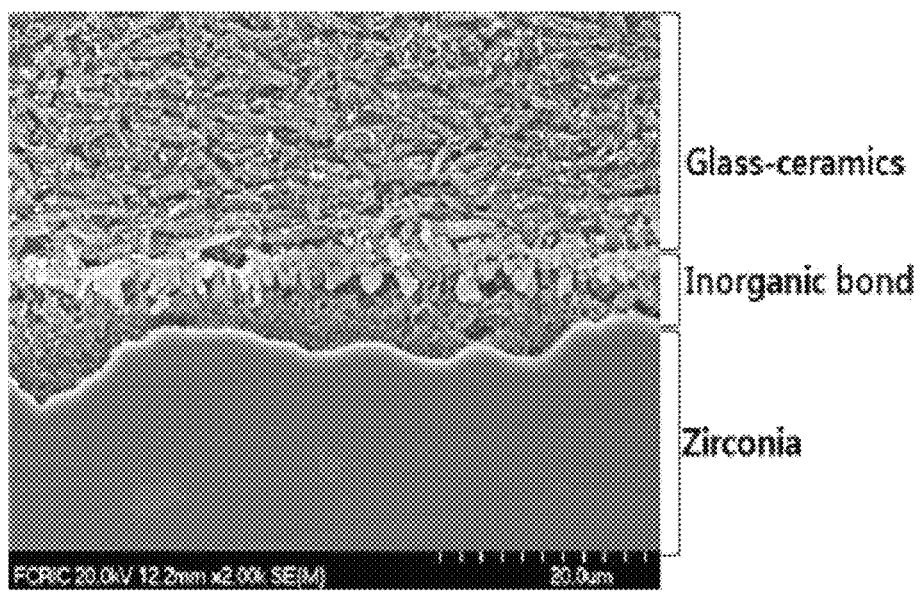
FIG. 3 illustrates a microstructure of a specimen in accordance with an exemplary embodiment.

FIG. 3 illustrates a microstructure after etching a bond interface. The inorganic bond may be formed with a uniform and dense structure between zirconia and the glass-ceramic, and while the specific component of the inorganic bond elutes zirconia, the chemical bond may be caused by forming a second crystalline occurrence.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A preparation method of a cristobalite crystalline lithium disilicate glass-ceramic, comprising:
    melting a glass-ceramic composition, comprising:
        10 to 15 wt % lithium oxide ($Li_2O$), 68 to 76 wt % silicon oxide ($SiO_2$), 2 to 5 wt % phosphorous pentoxide ($P_2O_5$), 0 to 5 wt % aluminum oxide ($Al_2O_3$), 2 to 3 wt % zirconium oxide ($ZrO_2$), 0.5 to 3 wt % calcium oxide (CaO), 0.5 to 5 wt % sodium oxide ($Na_2O$), 0.5 to 5 wt % potassium oxide ($K_2O$), and 1 to 2 wt % colorants, and 0 to 2.0 wt % of a mixture of magnesium oxide (MgO), zinc oxide (ZnO), fluorine (F), and lanthanum oxide ($La_2O_3$),
    crystallizing the glass-ceramic composition by performing a first crystallization heat treatment at 700° C. to 900° C. for 1 minute to 2 hours on the glass-ceramic composition, and
    crystallizing the glass-ceramic composition by performing a second crystallization heat treatment at 800° C. to 920° C. for 1 minute to 2 hours.

2. The preparation method of claim 1, wherein the lithium disilicate is formed by using a hyaline as a main component through the first crystallization heat treatment and the cristobalite crystal is formed by using the lithium disilicate crystalline through the second crystallization heat treatment.

3. A preparation method of a cristobalite crystalline lithium disilicate glass-ceramic, comprising:
    melting a glass-ceramic composition, comprising:
        10 to 15 wt % lithium oxide ($Li_2O$), 68 to 76 wt % silicon oxide ($SiO_2$), 2 to 5 wt % phosphorous pentoxide ($P_2O_5$), 0 to 5 wt % aluminum oxide ($Al_2O_3$), 2 to 3 wt % zirconium oxide ($ZrO_2$), 0.5 to 3 wt % calcium oxide (CaO), 0.5 to 5 wt % sodium oxide ($Na_2O$), 0.5 to 5 wt % potassium oxide ($K_2O$), and 1 to 2 wt % colorants, and 0 to 2.0 wt % of a mixture of magnesium oxide (MgO), zinc oxide (ZnO), fluorine (F), and lanthanum oxide ($La_2O_3$),
    crystallizing the glass-ceramic composition by performing a first crystallization heat treatment at 700° C. to 900° C. for 1 minute to 2 hours on the glass-ceramic composition, and
    bonding the glass-ceramic composition through the first crystallization heat treatment to a zirconia post at 700° C. to 900° C. for 1 minute to 2 hours with an inorganic bond.

4. The preparation method of claim 3, wherein the inorganic bond comprises 8 to 12 wt % lithium oxide ($Li_2O$), 50 to 75 wt % silicon oxide ($SiO_2$), 0 to 3 wt % aluminum oxide ($Al_2O_3$), 0.5 to 5 wt % calcium oxide (CaO), 0.5 to 3 wt % sodium oxide ($Na_2O$), 0.5 to 3 wt % potassium oxide ($K_2O$), 0.5 to 7 wt % phosphorous pentoxide ($P_2O_5$), 0.5 to 1 wt % colorant, and 0 to 1.0 wt % mixture of MgO, ZnO, F, and $La_2O_3$, and the thermal expansion coefficient is 9.5 to $10.8 \times 10^{-6}/°$ C.

* * * * *